United States Patent
Adams et al.

(10) Patent No.: US 10,982,113 B2
(45) Date of Patent: *Apr. 20, 2021

(54) COATING SYSTEM

(71) Applicant: DSM IP ASSETS B.V., Heerlen (NL)

(72) Inventors: Michael John Adams, Kaiseraugst (CH); Bruno Leuenberger, Kaiseraugst (CH); Loni Schweikert, Kaiseraugst (CH); Olivia Vidoni, Kaiseraugst (CH); Yan Zhang, Kaiseraugst (CH); Zhibing Zhang, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/763,532

(22) PCT Filed: Sep. 23, 2016

(86) PCT No.: PCT/EP2016/072686
§ 371 (c)(1),
(2) Date: Mar. 27, 2018

(87) PCT Pub. No.: WO2017/055184
PCT Pub. Date: Apr. 6, 2017

(65) Prior Publication Data
US 2018/0282579 A1 Oct. 4, 2018

(30) Foreign Application Priority Data

Oct. 2, 2015 (EP) .................................... 15188059

(51) Int. Cl.
| | | |
|---|---|---|
| C09D 191/06 | (2006.01) | |
| C08L 91/06 | (2006.01) | |
| A61K 9/20 | (2006.01) | |
| A61K 9/50 | (2006.01) | |
| C08G 65/332 | (2006.01) | |
| C08G 65/26 | (2006.01) | |

(52) U.S. Cl.
CPC .......... *C09D 191/06* (2013.01); *A61K 9/2095* (2013.01); *A61K 9/5015* (2013.01); *C08L 91/06* (2013.01); *C08G 65/2609* (2013.01); *C08G 65/3322* (2013.01)

(58) Field of Classification Search
CPC .. C09D 191/06; A61K 9/2095; A61K 9/5015; C08L 91/06
See application file for complete search history.

(56) References Cited

U.S. PATENT DOCUMENTS

| | | |
|---|---|---|
| 3,438,797 A | 4/1969 | Biddle |
| 5,662,732 A | 9/1997 | Kelley et al. |
| 5,891,476 A | 4/1999 | Reo et al. |
| 2009/0253801 A1* | 10/2009 | Shah ...................... A61K 9/284 514/652 |
| 2010/0104689 A1* | 4/2010 | Thorengaard ............ A23G 4/08 426/5 |

FOREIGN PATENT DOCUMENTS

| | | |
|---|---|---|
| JP | 54-143518 | 11/1979 |
| JP | 2000-063743 | 2/2000 |
| JP | 2006-523221 | 10/2006 |
| JP | 5 454 162 | 3/2014 |
| WO | WO 2014/017507 | 1/2014 |

OTHER PUBLICATIONS

International Search Report for PCT/EP2016/072686, dated Nov. 23, 2016, 3 pages.
Written Opinion of the ISA for PCT/EP2016/072686, dated Nov. 23, 2016, 4 pages.
Notice of Reasons for Rejection, Patent Appln No. P2018-515947 with English-Language Translation dated Jun. 9, 2020.

\* cited by examiner

*Primary Examiner* — Genevieve S Alley
(74) *Attorney, Agent, or Firm* — Nixon & Vanderhye P.C.

(57) ABSTRACT

The present patent application relates to a novel coating system, wherein the coating comprises Carnauba wax and at least one polysorbate. Furthermore it relates to compositions coated with such a coating system and the use of such compositions in the production of tablets.

6 Claims, 2 Drawing Sheets

COATING SYSTEM

Figure 1:
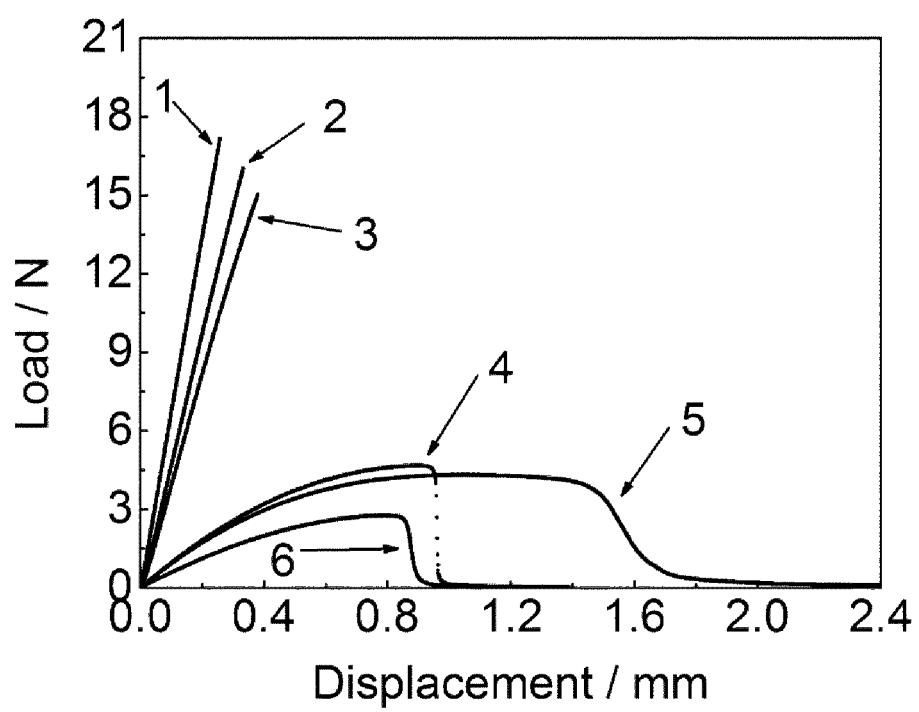

This application is the U.S. national phase of International Application No. PCT/EP2016/072686 filed 23 Sep. 2016, which designated the U.S. and claims priority to EP Patent Application No. 15188059.8 filed 2 Oct. 2015, the entire contents of each of which are hereby incorporated by reference.

The present patent application relates to a novel coating system, wherein the coating comprises Carnauba wax and at least one polysorbate. Furthermore it relates to compositions coated with such a coating system and the use of such compositions in the production of tablets.

Coating systems (or coatings) are used to protect particles against any kind of external influence. It is usually its goal to keep the particles as intact as possible. The particle can be of any size and shape. In the context of the present invention the particles (or cores), which are coated are small and they are pressed into a tablet (usually together with other useful components).

The problem with some coatings is that they are not suitable when the coated particles are designed to be used in compressed tablets. The main problem is that when the pressure is applied the coated particles are destroyed and the core (especially the active ingredient of the core) is exposed to the external influences.

When using Carnauba wax as such to coat particles, it might be too brittle for some applications and therefore it is well known to mix Carnauba wax with other waxes, such as for example with beeswax.

Also other mixtures, which are used nowadays are not sufficient for coating particles, which are then pressed into a tablet.

Therefore there is still a need for an improved coating system with excellent tablet pressing properties.

The goal of the present invention was to provide a coating system, which is especially suitable for particles, which are used in the production of (pressed) tablets.

Surprisingly it was found that when a mixture of Carnauba wax and at least one polysorbate is used as a coating then coated particles with excellent properties in regard to tablet pressing are obtained.

The term "compressed tablets" or "compacted tablets" (both terms mean the same) in the context of the present invention refers to tablet which are produced by applying pressure in their production.

Therefore the present invention relates to a new coating system (CS) comprising
(i) 50-95 weight-% (wt-%), based on the total weight of the coating system, of Carnauba wax and
(ii) 5-50 wt-%, based on the total weight of the coating system, of at least one compound of formula (I)

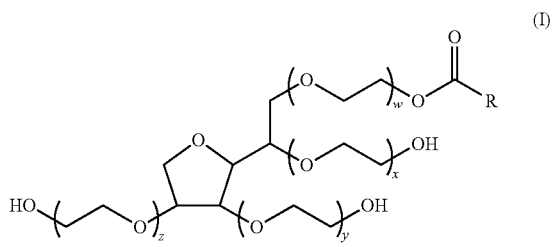

wherein
w, x, y and z are independently from each other integers which sum up to 20, and
R is a linear or branched $C_{10}$-$C_{18}$-alkyl moiety or a linear or branched $C_{10}$-$C_{18}$-alkylene moiety.

The sum of the wt-%'s always add up to 100.

The compounds of formula (I) are polysorbates.

Carnauba wax, also called Brazil wax and palm wax, is a wax of the leaves of the palm *Copernicia prunifera* (Synonym: *Copernicia cerifera*), a plant native to and grown only in the northeastern Brazilian states of Piauí, Ceará, and Rio Grande do Norte. In its pure state, it usually comes in the form of hard yellow-brown flakes. It is obtained from the leaves of the Carnauba palm by collecting and drying them, beating them to loosen the wax, then refining and bleaching the wax.

This epicuticular wax has a wide range of applications in products such as confectioneries, polishing wax, paints, and cosmetics. One of its many useful applications is in dentistry, where Carnauba wax can be used as an inlay casting composition and subsequently replaced by metal during casting. However, it is brittle in the native state at room temperature and is the hardest naturally occurring commercial wax.

Carnauba wax is available from many commercial suppliers (such as i.e. Sigma Aldrich,).

In a preferred embodiment the content of compound of formula (I) (and mixture thereof) in the coating system is 5-45 wt-%, based on the total weight of the coating system, more preferred 5-40 wt-%, based on the total weight of the coating system, especially preferred 5-30 wt-%, based on the total weight of the coating system, most preferred 5-20 wt-%, based on the total weight of the coating system.

In a preferred embodiment the content of the Carnauba wax in the coating system is 55-95 wt-%, based on the total weight of the coating system, more preferred 60-95 wt-%, based on the total weight of the coating system, especially preferred 70-95 wt-%, based on the total weight of the coating system, most preferred 80-95 wt-%, based on the total weight of the coating system.

Therefore the present invention relates to a coating system (CS1) which is coating system (CS), comprising 5-45 wt-%, based on the total weight of the coating system, of at least one compound of formula (I).

Therefore the present invention relates to a coating system (CS1') which is coating system (CS), comprising 5-40 wt-%, based on the total weight of the coating system, of at least one compound of formula (I).

Therefore the present invention relates to a coating system (CS1") which is coating system (CS), comprising 5-30 wt-%, based on the total weight of the coating system, of at least one compound of formula (I).

Therefore the present invention relates to a coating system (CS1''') which is coating system (CS), comprising 5-20 wt-%, based on the total weight of the coating system, of at least one compound of formula (I).

Therefore the present invention relates to a coating system (CS2) which is coating system (CS), (CS1), (CS1'), (CS1") or (CS1''') comprising 55-95 wt-%, based on the total weight of the coating system, of Carnauba wax.

Therefore the present invention relates to a coating system (CS2') which is coating system (CS), (CS1), (CS1'), (CS1") or (CS1''') comprising 60-95 wt-%, based on the total weight of the coating system, of Carnauba wax.

Therefore the present invention relates to a coating system (CS2") which is coating system (CS), (CS1), (CS1'), (CS1") or (CS1''') comprising 70-95 wt-%, based on the total weight of the coating system, of Carnauba wax.

Therefore the present invention relates to a coating system (CS2''') which is coating system (CS), (CS1), (CS1'), (CS1") or (CS1''') comprising 80-95 wt-%, based on the total weight of the coating system, of Carnauba wax.

In a preferred embodiment the compound of formula (I) is chosen from the group consisting of polysorbate 20, polysorbate 60 and polysorbate 80.

In a more preferred embodiment the compound of formula (I) is chosen from the group consisting of polysorbate 20 and polysorbate 60.

Therefore the present invention relates to a coating system (CS3) which is coating system (CS), (CS1), (CS1'), (CS1"), (CS1'''), (CS2), (CS2'), (CS2") or (CS2'''), wherein the compound of formula (I) is chosen from the group consisting of polysorbate 20, polysorbate 60 and polysorbate 80.

Therefore the present invention relates to a coating system (CS3') which is coating system (CS), (CS1), (CS1'), (CS1"), (CS1'''), (CS2), (CS2'), (CS2") or (CS2'''), wherein the compound of formula (I) is chosen from the group consisting of polysorbate 20 and polysorbate 60.

The coating system according to the present invention is produced by commonly known methods.

Usually the Carnauba wax is melted and the compound of formula (I) (or a mixture thereof) is added and then homogenised. The sequence of adding the various components is not essential for the invention.

The coating system according to the present invention is used to coat small particles (up to 1 mm), which are then used to be compacted into a tablet.

The coated particles are usually of such a size that tablets can be compacted.

A suitable size of the particles (=core) which are to be coated by the coating system according to the present invention is between 50-1000 µm (preferably 100-800 µm); the size is defined by the diameter of the longest dimension of the particle and measured by commonly known method (like light scattering).

The distribution of the particle size is also no essential feature of the present invention.

The shape of the core as well as of the coated particles is also not an essential feature of the present invention. The shape can be sphere-like or any other form (also mixtures of shapes). Usually and preferably the particles are sphere-like.

The particles can be produced by any commonly known process, which are used to produce such particles (spray drying, spray chilling, etc).

The process of coating such small particles is well known. It is usually done by fluidized bed spray granulation, film coating or wet granulation.

The present invention also relates to particles coated with a coating system (CS), (CS1), (CS1'), (CS1"), (CS1'''), (CS2), (CS2'), (CS2"), (CS2'''), (CS3) or (CS3').

Usually the thickness of the coating layer is 5-30 µm. It is clear that the coating layer is usually not equally thick when applied onto the particle. But the variation of the thickness is usually not huge.

Usually the coated particle consists of 40-95 wt-%, based on the total of the coated particle, of core and 5-60 wt-%, based on the total weight of the particle of coating layer according to the present invention.

Therefore the present invention also relates to a coated particle (CP), which consists of 45-95 wt-%, based on the total of the coated particle, of core and 5-55 wt-%, based on the total weight of the particle of coating layer (CS), (CS1), (CS1'), (CS1"), (CS1'''), (CS2), (CS2'), (CS2"), (CS2'''), (CS3) or (CS3').

It is possible to produce the particles first and then coat them at a later stage or to do both steps in one process (production of particles and then coating).

The particle usually comprises at least one active ingredient, which is needed in the pressed tablet or in any other formulation form (which is the end-product).

That active ingredient (or mixture of active ingredients) can be any kind of ingredient. The ingredients can be oil-soluble/or water-soluble.

Suitable ingredients are i.e. any vitamins, carotenoids, minerals, plant extracts or any other active ingredient.

Suitable ingredients are fat-soluble vitamins, such a vitamin A, D, E, and K (as well as derivatives thereof); water-soluble vitamins such as vitamin B and C; and carotenoids such as α-carotene, β-carotene, 8'-apo-β-carotenal, 8'-apo-β-carotenoic acid esters, canthaxanthin, astaxanthin, lycopene, lutein, zeaxanthin and crocetin.

The amount of the active ingredient in the core can vary. The amount be up to 75-wt-%, based on the total weight of the core, of at least one active ingredient. Usually the core comprise at least 5 wt-%, based on the total weight of the core, of at least one active ingredient.

A very usual range of an amount of the active ingredient in the core is from 5-40 wt-%, based on the total weight of the core.

Another very usual range of an amount of the active ingredient in the core is from 5-20 wt-%, based on the total weight of the core.

Therefore the present invention relates to a coated particle (CP1), which is coated particle (CP), wherein the amount of the at least one active ingredient in the core is up to 75 wt-%, based on the total weight of the core.

Therefore the present invention relates to a coated particle (CP1'), which is coated particle (CP), wherein the amount of the at least one active ingredient in the core is at least 5 wt-%, based on the total weight of the core.

Therefore the present invention relates to a coated particle (CP1"), which is coated particle (CP), wherein the amount of the at least one active ingredient in the core is 5 wt-%-40 wt-%, based on the total weight of the core.

Therefore the present invention relates to a coated particle (CP1'''), which is coated particle (CP), wherein the amount of the at least one active ingredient in the core is 5 wt-%-20 wt-%, based on the total weight of the core.

The coated particles according to the present invention are used in the production of food, feed, pharma and/or personal care applications.

Preferably they are used in the production of compressed tablets. The compressed tablets can be for the pharma market as well as for the nutrition market.

It is also possible to produce premixes for food, feed, pharma and/or personal care applications, which are then used to form the final application formulation.

The amount of the active ingredient(s) in compressed tablets according to the present invention can be influenced and controlled by the amount of the at least active ingredient in the core and by the amount of core in relation to coating and finally the amount of the coated particle in the process of production of the compressed tablet.

Therefore the present invention relates to the use of the coated particles (CP), (CP1), (CP1'), (CP1") or (CP1'") in the production of food, feed, pharma and/or personal care application.

Therefore the present invention relates to the use of the coated particles (CP), (CP1), (CP1'), (CP1") or (CP1'") in the production of compressed tablets.

The present invention also relates to the process for the production (P) of compressed tablets using the coated particles (CP), (CP1), (CP1'), (CP1") or (CP1'"), wherein a pressure of at least 5 kN is applied.

To produce compress tablets a pressure of 5-40 kN is usually applied.

Therefore the present invention relates to a process (P1), which is process (P), wherein a pressure of 5-40 kN usually applied.

The particle comprises usually other components, which are useful for the particle and/or food, feed, pharma and/or personal care products or the compacted tablet.

The obtained tablets are storage stable. This means that the content of the ingredient in pressed tablet is more or less at a constant level over a longer time period.

The present invention also relates to compressed tablets (CT) comprising
(i) 0.1-40 wt-%, based on the total weight of the compressed tablets, of the coated particles CP), (CP1), (CP1'), (CP1") or (CP1'"), which comprise 40 wt-%-95 wt-%, based on the total weight of the coated particle, of a core, comprising at least one active ingredient and 5 wt-%-60 wt-%, based on the total weight of the coated particle, of a coating system, and said coating system comprises at least one wax and/or at least one fat,
and
(ii) 60-99.1 wt-%, based on the total weight of the compressed tablets, of at least one additional ingredient, excipient and/or auxiliary agent chosen from the group consisting of fillers (such as microcrystalline cellulose), acidity regulators (such as calcium phosphate), anti-adherent (such as magnesium stearate), dyes, flavours and sweeteners.

All preferences defined above for the coated particles used in the process according to the present invention also relates to the compressed tablets defined herein.

The present invention also relates to compressed tablets (CT1) comprising
(i) 0.1-40 wt-%, based on the total weight of the compressed tablets, of the coated particles CP), (CP1), (CP1'), (CP1") or (CP1'"), which comprise 40 wt-%-95 wt-%, based on the total weight of the coated particle, of a core, comprising vitamin A and/or its derivative and 5 wt-%-60 wt-%, based on the total weight of the coated particle, of a coating system consisting of carnauba wax, candelilla wax, sugarcane wax and/or (fully) hydrogenated palm oil,
and
(ii) 60-99.1 wt-%, based on the total weight of the compressed tablets, of at least one additional ingredient, excipient and/or auxiliary agent chosen from the group consisting of fillers (such as microcrystalline cellulose), acidity regulators (such as calcium phosphate), anti-adherent (such as magnesium stearate), dyes, flavours and sweeteners.

FIGURES

FIG. 1.: Shows the results of the mechanical stability (flexural test) of the various coating systems. 1=pure Carnauba wax, 2=Carnauba wax+30 w/w % Span® 65, 3=Carnauba wax+30 w/w % beeswax, 4=Carnauba wax+30 w/w % polysorbate 20, 5=Carnauba wax+30 w/w % polysorbate 60, 6=Carnauba wax+30 w/w % polysorbate 80

Figure 2:
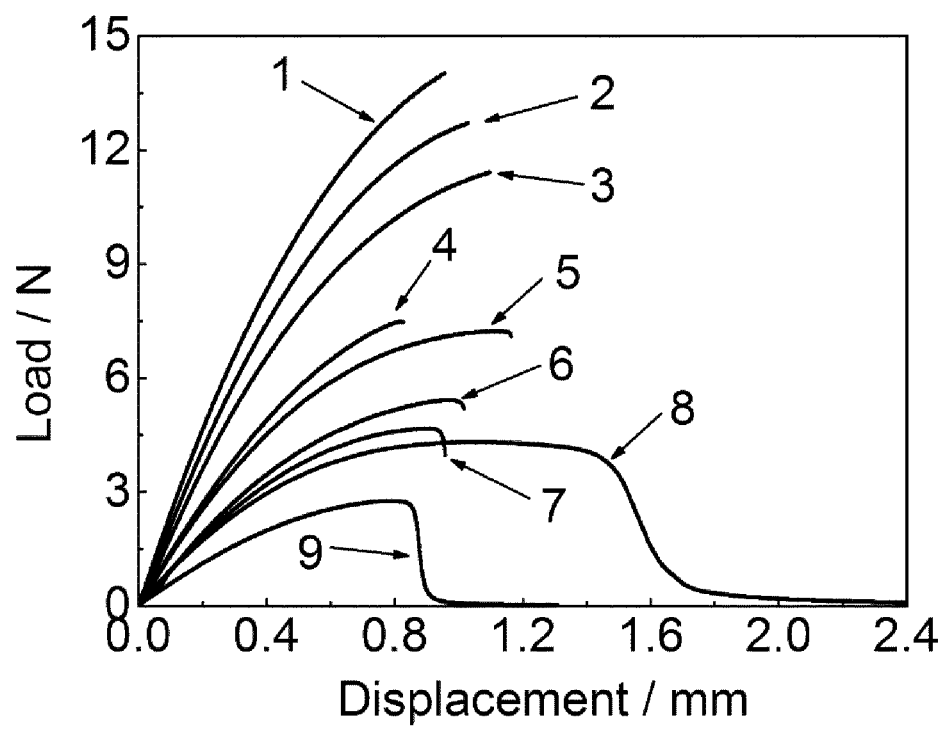

FIG. 2.: Shows the results of the mechanical stability of the various coating systems, 1=Carnauba wax+10 w/w % polysorbate 60, 2=Carnauba wax+10 w/w % polysorbate 80, 3=Carnauba wax+10 w/w % polysorbate 20 (CW+30% PS80), 4=Carnauba wax+20 w/w % polysorbate 80, 5=Carnauba wax+20 w/w % polysorbate 60, 6=Carnauba wax+20 w/w % polysorbate 20 (CW+30% PS80); 7=Carnauba wax+30 w/w % polysorbate 80, 8=Carnauba wax+30 w/w % polysorbate 60, 9=Carnauba wax+30 w/w % polysorbate 20 (CW+30% PS80)

The invention is illustrated by the following Example. All temperatures are given in ° C. and all parts and percentages are related to the weight.

EXAMPLES

The coating systems in all the following examples were produced in the same way: A heating plate (C-MAG HS 7 from IKA) was used to melt the Carnauba wax as well as the compound of formula (I) or the other ingredients (comparative examples). The ingredients were added into a vessel an then heated up to 120° C. All mixtures were homogenised with an Labortechnik Eurostar stirrer (from IKA) at 500 rpm for 5 min.

The various mixtures as well as the pure Carnauba wax were tested in regard to its mechanical stability, which is an important criteria for a coating system.

Example 1 (Flexural Test)

For the first series of examples a mixture of 70 wt-% of Carnauba wax and 30 wt-% of different plasticizers were produced. Table 1 shows the plasticizers which have been used

TABLE 1

| Example | Plastizers | Amount [wt-%] |
| --- | --- | --- |
| 1a (Comparison test) | — | 0 |
| 1b (Comparison test) | Span 65 | 30 |
| 1c (Comparison test) | Beeswax | 30 |
| 1d (Invention) | Polysorbate 20 | 30 |
| 1e (Invention) | Polysorbate 60 | 30 |
| 1f (Invention) | Polysorbate 80 | 30 |

Span 65 ® is the compound of the following formula

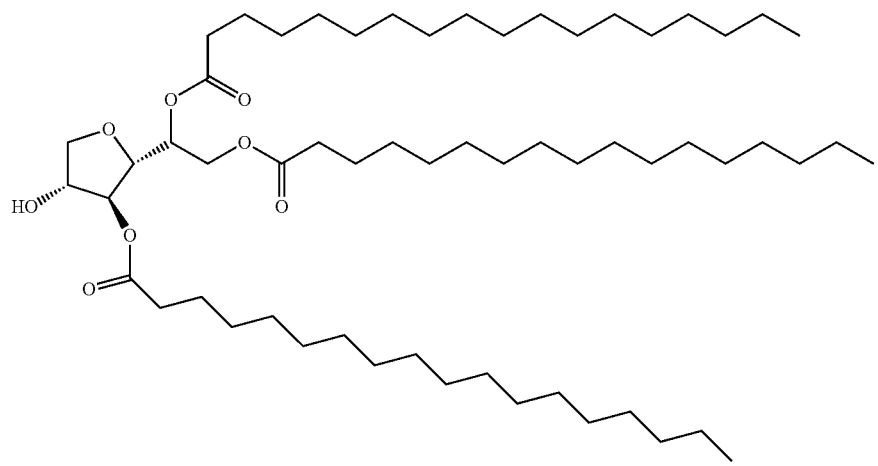 [SMILES: CCCCCCCCCCCCCCCCCC(=O)OC(COC(=O)CCCCCCCCCCCCCCCC)[C@H]1OC[C@@H](O)[C@@H]1OC(=O)CCCCCCCCCCCCCCCCC]

The specimens for flexural measurements were moulded into a cylindrical shape using 1 ml BD Plastipak Luer syringes with their tips cut off. To prevent poor flowability of the melted wax mixtures caused by solidification while cooling in contact with the syringes, they were heated to 120° C. in an oven before the moulding process. The homogenised melted mixtures were subsequently poured into the syringes and equilibrated at the laboratory temperature controlled at 17° C. to allow solidification. The moulded specimens were afterwards pushed out of the syringes and those with observable cracks were discarded. For each sample, 5 replicates were prepared. The diameter and length of the specimens were measured with a digital calliper (resolution 0.01 mm) to be 4.56±0.07 and 55.35±1.50 mm.

Mechanical tests were performed on an Instron 5848 MicroTester with a 100 N load cell. The position resolution is 0.02 μm for speeds of <200 mm/min. The actuator speed accuracy at zero or constant load is ±0.1% of the set speed. The accuracy of the load cell is 0.025 N when the load is ≤10 N, and 0.25% of the indicated load when it is >10 N. An Instron 3-point bend configuration was used for the flexure tests. The radius of both the top and bottom anvils was 1.0 mm. The span between the lower two anvils was 30 mm. The loading speed was set to 0.05 mm/s. The compliance of the system including the flexure fixture tooling was measured to be 0.872 μm/N. For the indentation tests, a spherical glass indenter with a diameter of 6.35 mm was utilised and the loading speed was 0.01 mm/s. The compliance of the system including the tooling for the indentation test was measured to be 1.167 μm/N.

The results of this test are summarised in FIG. 1.

It can be seen that the mixtures which comprise polysorbate are significantly better.

Example 2

In the following tests various mixtures of Carnauba wax with different amounts of polysorbates were tested. The testing conditions were the same as in Example 1

TABLE 2

| Example | Plastizers | Amount [wt-%] |
|---------|------------|---------------|
| 2a | Polysorbate 60 | 10 |
| 2b | Polysorbate 80 | 10 |
| 2c | Polysorbate 20 | 10 |
| 2d | Polysorbate 80 | 20 |
| 2e | Polysorbate 60 | 20 |
| 2f | Polysorbate 20 | 20 |
| 2g | Polysorbate 80 | 30 |
| 2h | Polysorbate 60 | 30 |
| 2i | Polysorbate 20 | 30 |

When the plasticiser concentration is 10 w/w %, the fracture surfaces of all specimens seem to be uniform, as shown in FIG. 2.

When the plasticiser concentration is increased to 20 w/w %, the fracture surface roughness starts varying from region to region, as shown in FIG. 2.

When the plasticiser concentration is further increased to 30 w/w %, the fracture surface roughness for polysorbate 20 and 60 modified specimens is greater than that of polysorbate 80. This suggests that the plasticising effect of polysorbate 80 is inferior to polysorbate 20 and 60.

The invention claimed is:

1. A method of making compacted tablets comprising:
   (a) providing coated particles consisting of, based on total weight of the coated particles, 40-95 wt. % of a core and 5-60 wt. % of a coating layer consisting of a coating system which coats the core, wherein the coating system consists of:
      (i) 70-90 wt. %, based on total weight of the coating system, of Carnauba wax, and
      (ii) 10-30 wt. %, based on total weight of the coating system, of at least one compound selected from the group consisting of polysorbate 20, polysorbate 60 and polysorbate 80, and thereafter
   (b) compacting the coated particles provided according to step (a) at a compaction pressure of at least 5 kN to form the compacted tablets.

2. The method according to claim 1, wherein the compaction pressure of step (b) is 5-40 kN.

3. The method according to claim 1, wherein the at least one compound selected from the group consisting of polysorbate 20, polysorbate 60 and polysorbate 80 is present in an amount of 10-20 wt-%, based on the total weight of the coating system.

4. The method according to claim 1, wherein the Carnauba wax is present in the coating system in an amount of 80-90 wt-%.

5. The method according to claim 1, wherein the core comprises at least one active ingredient.

6. The method according to claim 5, wherein the active ingredient is at least one selected from the group consisting of vitamins, carotenoids, minerals and plant extracts.

* * * * *